(12) United States Patent
Heronen (10) Patent No.: US 11,187,262 B2
(45) Date of Patent: Nov. 30, 2021

(54) HINGE HAVING A ROTATION-STOP LOCK

(71) Applicant: Ossur Iceland ehf, Reykjavik (IS)

(72) Inventor: Nathan Heronen, Foothill Ranch, CA (US)

(73) Assignee: OSSUR ICELAND EHF, Reykjavik (IS)

( * ) Notice: Subject to any disclaimer, the term of this patent is extended or adjusted under 35 U.S.C. 154(b) by 0 days.

(21) Appl. No.: 16/710,270

(22) Filed: Dec. 11, 2019

(65) Prior Publication Data

US 2020/0182287 A1 Jun. 11, 2020

Related U.S. Application Data

(60) Provisional application No. 62/778,225, filed on Dec. 11, 2018.

(51) Int. Cl.
*F16C 11/04* (2006.01)
*A61F 5/01* (2006.01)
*E05D 11/10* (2006.01)

(52) U.S. Cl.
CPC ............ *F16C 11/04* (2013.01); *A61F 5/0102* (2013.01); *E05D 11/10* (2013.01); *E05D 11/1007* (2013.01); *A61F 2005/0155* (2013.01); *A61F 2005/0167* (2013.01)

(58) Field of Classification Search
CPC .... A61F 5/1023; A61F 5/0106; A61F 5/0167; E05D 11/1007; Y10T 16/54035; Y10T 16/54038
See application file for complete search history.

(56) References Cited

U.S. PATENT DOCUMENTS

| | | | |
|---|---|---|---|
| 4,732,143 A | 3/1988 | Kausek et al. | |
| 6,438,798 B1 * | 8/2002 | Chene | G02C 5/2254 16/284 |
| 6,817,064 B2 * | 11/2004 | Kim | E05D 11/105 16/335 |
| 7,235,058 B2 | 6/2007 | Doty et al. | |
| 7,320,672 B2 | 1/2008 | Turrini et al. | |
| 7,544,174 B2 | 6/2009 | Nathanson | |

(Continued)

FOREIGN PATENT DOCUMENTS

DE 102010045469 A1 3/2012
DE 102016010241 A1 3/2018

(Continued)

OTHER PUBLICATIONS

"Bledsoe Axiom/Axiom-D Custom & OTS Knee Brace," Bledsoe Brace Systems, Jan. 2007.
"Tool Free Hinge Research," Patrick Kiruki, May 4, 2018.

*Primary Examiner* — Victor D Batson
*Assistant Examiner* — Matthew J Sullivan
(74) *Attorney, Agent, or Firm* — Workman Nydegger (57) ABSTRACT

A hinge is configured for selectively retaining and removing at least one rotation stop without a supplementary tool. The hinge includes a locking device having at least one lever arranged to selectively rotate a retaining member for engagement and disengagement with the at least one rotation stop. The retaining member forms an abutment portion extending from a first portion and a second portion extending from the abutment portion. A non-abutment portion is located opposite the abutment portion along a same segment of the axis of the retaining member.

17 Claims, 8 Drawing Sheets

(56) References Cited

U.S. PATENT DOCUMENTS

| | | | |
|---|---|---|---|
| 7,841,999 B2* | 11/2010 | Napholz | A61F 5/0123 602/16 |
| 7,887,496 B2 | 2/2011 | Kahlmeyer et al. | |
| 8,105,255 B2 | 1/2012 | Panzer et al. | |
| 8,157,756 B2 | 4/2012 | Schimek et al. | |
| 8,187,211 B2 | 5/2012 | Chiang et al. | |
| 8,628,486 B2 | 1/2014 | Ferrigolo et al. | |
| 8,914,946 B2* | 12/2014 | Hsu | F16H 21/44 16/366 |
| 8,920,349 B2 | 12/2014 | Ferrigolo et al. | |
| 9,668,903 B2 | 6/2017 | Hsu et al. | |
| 9,872,791 B2 | 1/2018 | Ferrigolo et al. | |
| 9,889,036 B2 | 2/2018 | Chiang et al. | |
| 10,596,022 B2* | 3/2020 | Turrini | A61F 5/0102 |
| 10,758,392 B2* | 9/2020 | Mason | A61F 5/0123 |
| 2015/0038889 A1 | 2/2015 | Mason et al. | |
| 2016/0038327 A1 | 2/2016 | Mason et al. | |
| 2017/0367867 A1* | 12/2017 | Nathanson | E05D 11/0054 |
| 2019/0151133 A1* | 5/2019 | Lee | A61F 5/0123 |
| 2019/0167461 A1* | 6/2019 | Turconi | A61F 5/0102 |

FOREIGN PATENT DOCUMENTS

| | | |
|---|---|---|
| EP | 1086672 A2 | 3/2001 |
| WO | 2017041993 A1 | 3/2017 |

\* cited by examiner

HINGE HAVING A ROTATION-STOP LOCK

FIELD OF THE DISCLOSURE

The present disclosure generally relates to a hinge for orthopedic devices. The hinge has a rotation-stop lock precluding need for using a supplementary tool to lock and unlock a rotation stop from the hinge.

BACKGROUND

Many types of orthopedic devices include hinges that support joints, and control and limit joint movements. These joints include, for example, the knee, elbow, shoulder, hip, ankle and wrist joints.

The knee joint comprises two joints, lateral and medial, between the femur and tibia, and one gliding or arthrodial joint between the patella and femur. The primary movements of the knee comprise flexion (i.e., rearward rotational movement of the tibia relative the femur), and extension (i.e., forward rotational movement of the tibia relative the femur), about centers or axes over an arc of about 180 degrees.

The flexion and extension movements of the knee joint are not simply pivotal movements about a fixed axis. During flexion, the axis around which movement takes place shifts backward, and during extension the axis shifts forward. This differs from a more typical hinge joint, such as an elbow, where the axis of rotation does not shift. As full extension is reached, the tibia is rotated inward or rearward and the joint, in effect, is disposed in a "locked" position with the ligaments taut. This gives the joint greater stability in the extended position such as when a person is standing or in a heel-strike phase of walking. As flexion is initiated, the tibia initially lowers or moves downwardly, with small external rotation of the tibia serving to unlock the joint, and subsequently the tibia rotates or rolls about the joint to full flexion. The initial unlocking of the knee joint during flexion precedes actual full rotation of the knee.

Because of the complexity associated with knee movement, a hinge in an orthopedic device must be able to simulate the dynamic movements of the knee. Incorporating such hinge mechanism is crucial, as the knee brace supports the knee joint of its user.

In post-surgical applications, the requirement for such simulation of the knee joint is essential to rehabilitate and prevent re-injury of an injured knee joint. The hinge mechanism should be able to control the range of knee joint flexion and extension so the knee is not reinjured due to hyperextension or flexion. As the optimal range of knee joint motion may vary between users and change during the progress of rehabilitation, the knee brace hinge mechanism used with such post-surgical applications should further be adjustable to correspond to the proper motion range of the user's leg.

In recognizing the need for an effective post-surgical knee brace, various types of hinge mechanisms have been incorporated into known knee braces for post-surgical applications. However, most conventional hinge mechanisms typically fail to precisely simulate knee joint movement or properly control the range of knee joint motion. Such deficiencies inevitably prevent the user's knee joint from being properly rehabilitated after surgery. Importantly, some known knee brace hinge mechanisms fail to possess sufficient adjustability to quickly and easily provide the optimal range of knee motion depending upon the user's current needs and rehabilitation progress.

Because of the shortcomings of conventional knee brace hinge mechanisms, there exists a need in the art for a hinge that can closely simulate the motion of the knee joint while easily and accurately regulating the range of its flexion and extension. It is desirable to provide a hinge system that can be easily and quickly adjusted to provide a variable, optimal range of knee joint flexion and extension based on the needs of its user.

While means for adjusting flexion and extension control with different stops according to degrees of rotation exist, such means often requires disassembly of a hinge with tools. Disassembly may lead to reassembly that conflicts with proper functioning of the hinge, or poorly installed stops particularly when performed by a user with limited dexterity or familiarity with the mechanisms of the hinge. The requirement of the use of a tool inhibits the ability to quickly replace and install different stops as desired, particularly if a tool is unavailable. These known means may also lack features that assure proper placement of the rotation stop relative to the hinge and support members or struts.

The features of the disclosure are provided in recognition of the need for hinges that are streamlined, low profile, and easy to adjust while supporting joints, and for controlling and limiting joint movement in a safe, repeatable and stable manner. This recognition is realized with the hinge embodiments described.

SUMMARY

A hinge is provided with a rotation stop lock precluding a need for using a supplementary tool to lock and unlock a rotation stop from the hinge. The hinge is tool-free or toolless because it has a locking device built-in or provided integrally with the hinge that permits selective engagement with a rotation stop in a safe, repeatable and stable manner. A kit of rotation stops for precise and controlled flexion and/or extension of the hinge is provided that can be selected according to desired range of motion of the hinge and installed in the hinge without disassembly of the hinge.

According to an embodiment, a hinge according to the disclosure includes a first plate having at least one lever recess defined along an outer surface of the first plate and a locking device having at least one lever arranged to selectively rotate a retaining member for engagement and disengagement with at least one rotation stop. The retaining member forms an abutment portion extending from a first portion and a second portion extending from the abutment portion. The first portion, the abutment portion and the second portion extend coaxial relative to one another along an axis of the retaining member. The rotation stop may have an opening defining a receiving section and a passage section extending from the receiving section to open along a periphery of the rotation stop. The passage section preferably is more narrow than the receiving section.

The abutment portion of the retaining member defines an abutment profile protruding outwardly at least a length beyond the first portion and the second portion about at least one segment of a periphery of the abutment portion. The abutment portion defines a non-abutment profile located outside the abutment profile in at least another segment of the periphery of the abutment portion and defines a width generally commensurate to a width of the first and second portions. The non-abutment portion is located opposite the abutment portion along a same segment of the axis of the retaining member.

The narrow passage section of the rotation stop may be configured and dimensioned to permit passage of the abutment portion to slide therethrough when the non-abutment profile is aligned to the passage section in a first configuration of the locking device. When the abutment portion is rotated relative to the first configuration to a second configuration, the abutment profile prevents sliding of the abutment portion relative to the passage section. The abutment profile may be configured and dimensioned differently from the non-abutment profile and is arranged to be received by the receiving section of the rotation stop.

These and other features of the present disclosure will become better understood regarding the following description, appended claims, and accompanying drawings.

The drawing figures are not necessarily drawn to scale, but instead are drawn to provide a better understanding of the components, and are not intended to be limiting in scope, but to provide exemplary illustrations. The figures illustrate exemplary configurations of a hinge, and in no way limit the structures or configurations of a hinge according to the present disclosure.

DETAILED DESCRIPTION OF VARIOUS EMBODIMENTS

In the embodiments provided herein, the hinge is provided as a tool-free or toolless range-of-motion hinge. By tool-free or toolless, it is understood that the range of motion of the hinge may be adapted without a supplementary tool such as a screwdriver, wrench, etc. Further, the hinge itself offers a mechanism by which a clinician or user can adjust the range of motion of the hinge without disassembly of the hinge, and such mechanism forms part of the hinge without interfering with the normal operation of the hinge.

According to the embodiments provided herein, rotation stops are provided and correspond to a plurality of different degrees of range of motion. One rotation stop may be insertable into the hinge to cause only 15 degrees of flexion, for example, whereas another rotation stop may permit 30 degrees of extension. It is not essential to the disclosure the specific degrees of rotation, but rather there is at least one rotation stop for modifying the range of motion of the hinge in either flexion or extension motion to a desired degree. The rotation stop is arranged to limit movement of the struts relative to one another and may have a geometry that limits such movement of the struts relative to one another according to a prescribed range of motion.

The embodiments of the hinge in this disclosure are associated with a polycentric hinge whereby joint members or struts have or are connected to mutually engaging toothed sectors at their adjacent ends and are pivotally mounted on respective ones of a pair of spaced, parallel tubular pivot pins. The pivot pins extend between and pivotally mount the adjacent ends of the joint members between side plates. The rotation stops may be inserted in a space defined between the side plates and snugly retained generally with the space. The rotation stops are not limited to being located or solely located within the space, but may be located otherwise in any suitable manner that limits or controls range of motion of the struts relative to one another.

While a polycentric hinge is described as an exemplary arrangement of a hinge according to which a tool-free or toolless mechanism may be provided for removably securing rotation stops as described herein, the locking device according to these embodiments may be extended to other forms of hinges. These other forms of hinges include four-bar hinges or other suitable hinges used in combination with struts upon or to which rotation stops may abut according to a predetermined range of motion of the hinge.

Figure 1:
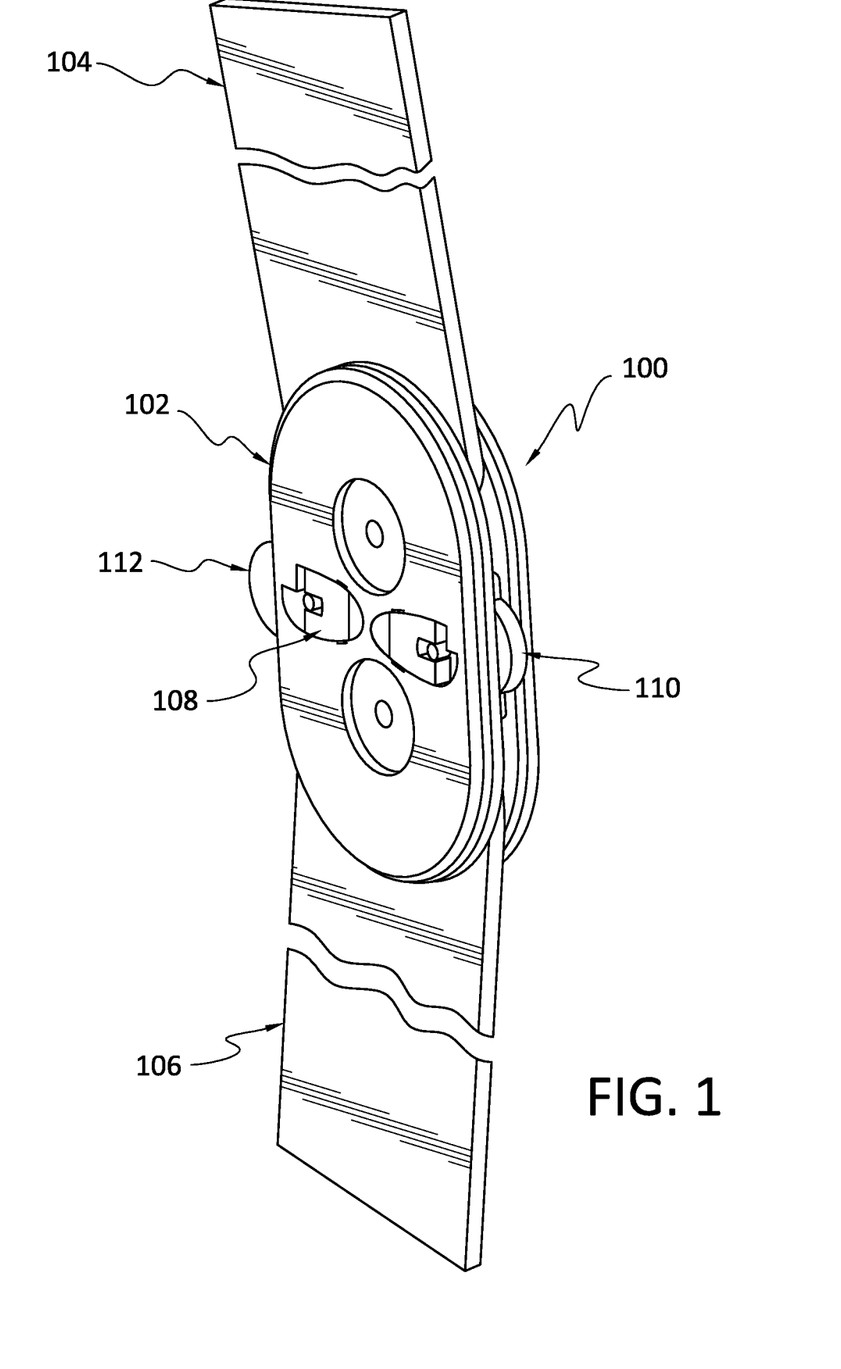
FIG. 1 is a perspective view illustrating an embodiment of a hinge according to the present disclosure.

In the exemplary embodiment of FIG. 1, the hinge 100 comprises a hinge assembly 102 arranged between and connecting a first or upper strut 104 and a second or lower strut 106. A locking device 108 is provided with the hinge assembly 102 and allows a user or a clinician to define a range of motion, in either flexion or extension, of the hinge 100 without the need to disassemble the hinge 100 or use a dedicated or supplementary tool, as explained above referring to tool-free or toolless range-of-motion adjustment.

The locking device 108 may cooperate with at least one rotation stop, such as first and second rotation stops 110, 112, which limit a range of motion, particularly in flexion and extension, respectively, of the first strut 104 relative to the second strut 106. The locking device 108 may be configured to receive the first and/or second rotation stops 110, 112 in an unlocked configuration, and then lock the first and/or second rotation stops 110, 112 in a locked configuration, allowing the first and/or second rotation stops 110, 112 to engage the struts 104, 106 depending on rotation of the hinge 100, and limiting movement in a predetermined manner. The locking device 108 may advantageously be configured, as shown in FIG. 1, in an unobtrusive manner when in use so as to maintain a low profile of the hinge while maintaining the locked configuration.

Figure 2:
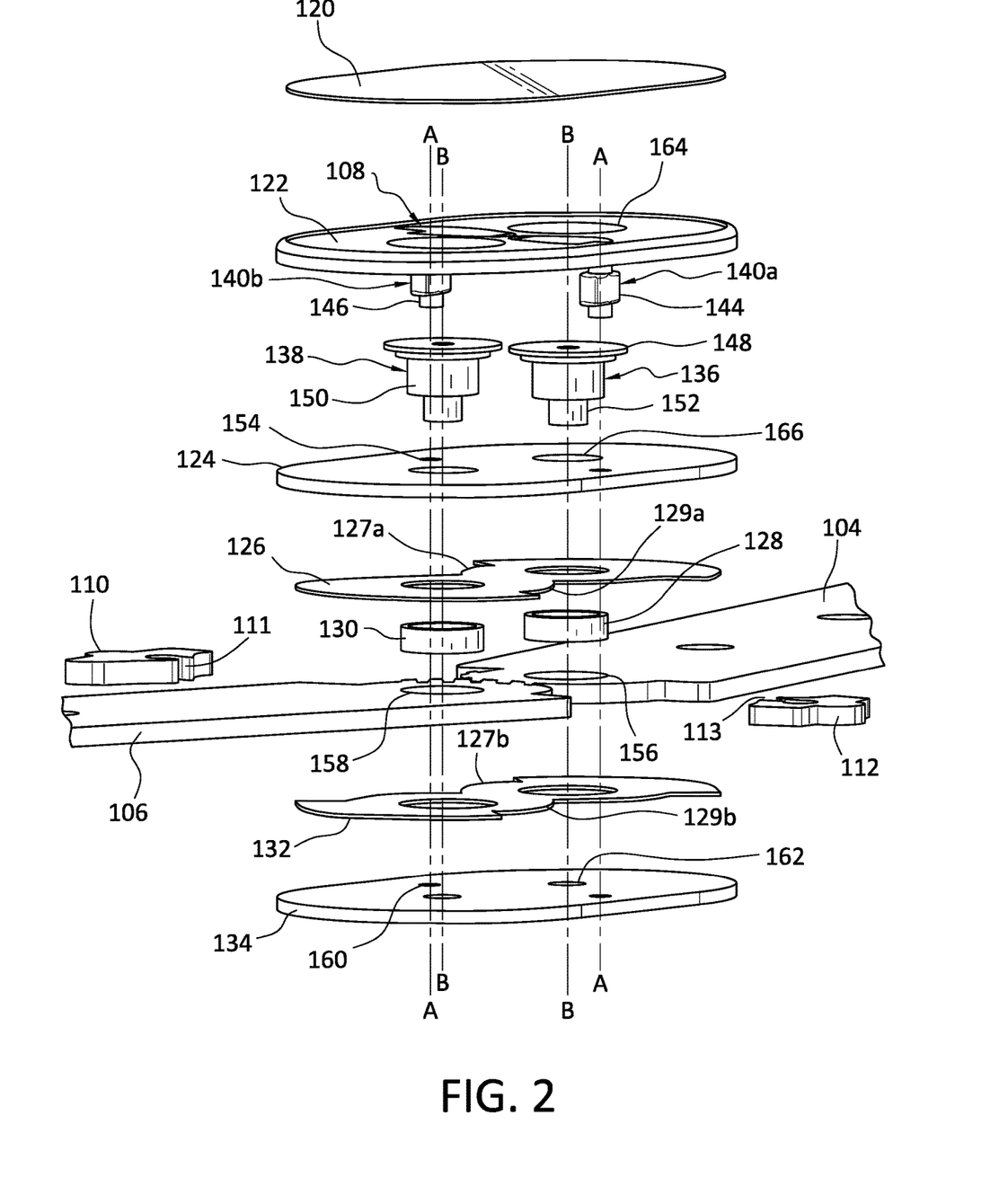
FIG. 2 is an exploded view of the hinge in FIG. 1.

FIG. 2 depicts an exploded view the hinge 100 of FIG. 1. A cover 120 is provided on an outermost or outward-facing first side of the hinge 100, concealing and/or protecting the components of the hinge 100 including the locking device 108. The hinge 100 can be provided with or without the cover 120.

Beneath or adjacent to the cover 120 is a first or outer side plate 122. The first plate 122 may cooperate with an internal plate 124. The first plate 122 may define seated openings 164 configured to receive first and second rivets or pivot pins 136, 138. First and second retaining members 140a, 140b may be adapted to move and secure relative to an outer surface of the first plate 122. The internal plate 124 may be arranged stacked against or adjacent to an inner surface of the first plate 122 so the retaining members 140a, 140b rotate relative to the internal plate 124. The first plate 122 and the internal plate 124 may be formed as a single plate having features for receiving the retaining members 140a, 140b and pivot pins 136, 138 with recesses and openings for operative engagement and retention therewith.

Figures 5A, 5B, 5C:
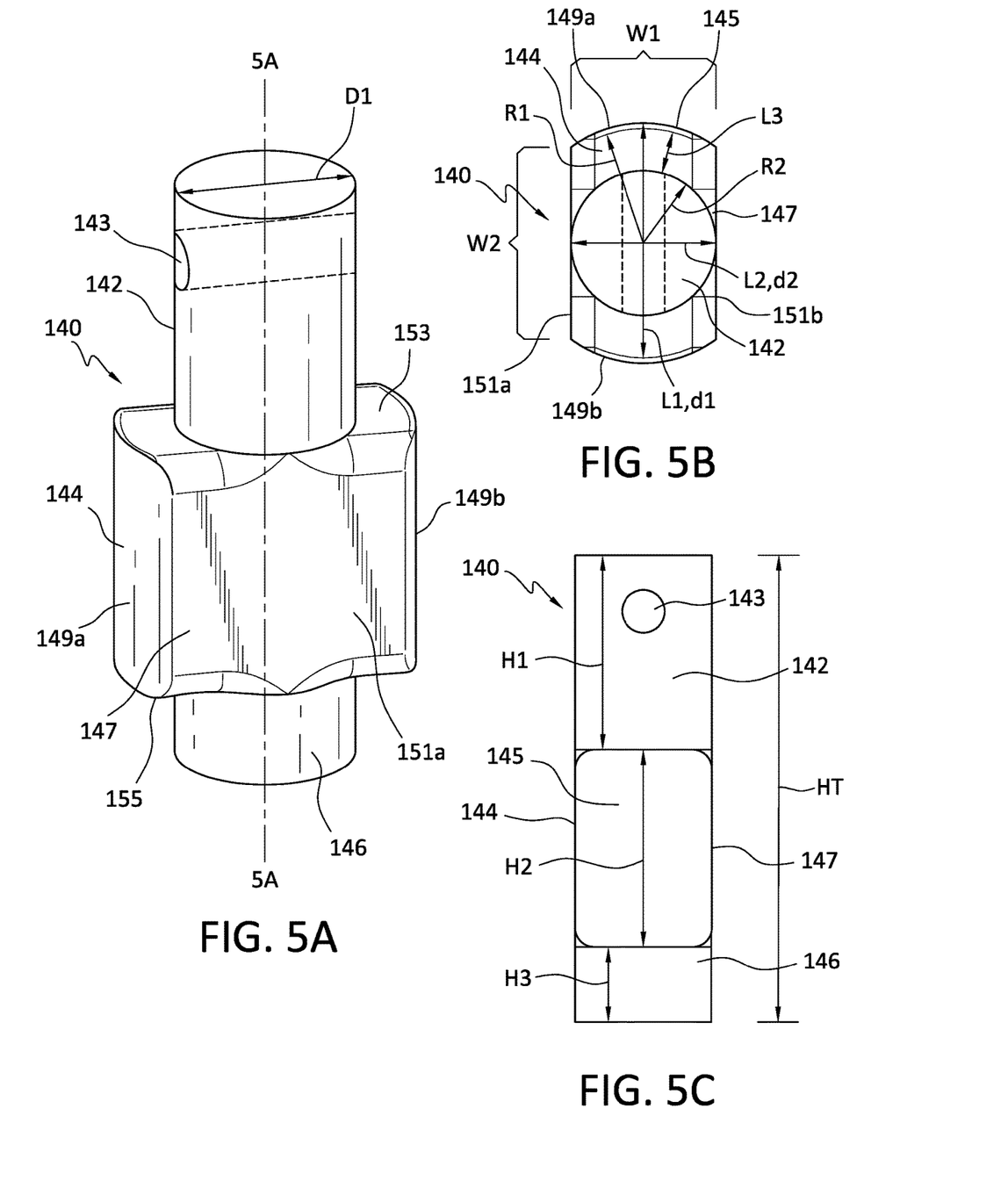
FIG. 5A is a perspective view of a retaining member in the hinge of FIG. 1.
FIG. 5B is a top plan view of the retaining member of FIG. 5A.
FIG. 5C is an elevational view of a first side of the retaining member of FIG. 5A.

As shown in better detail in FIGS. 5A-5C, the first and second retaining members 140a, 140b may comprise an upper or first portion 142 that passes through the first and internal plates 122, 124. An abutment portion 144 extends from the first portion 142, and a lower or second portion 146 extends from the abutment portion 144. The abutment portion 144 preferably is sized to the space defined between the internal plate 124 and the second plate 134, whereas the first portion 142 may extend through or within a combined thickness or at least part of a thickness defined by the first plate 122 and the internal plate 124, and the lower portion 134 may extend in at least part of a thickness of the second plate 134.

The first and second pivot pins 136, 138 may comprise a head 148 located at an outermost or outward-facing end of the pivot pins 136, 138, a cylinder 150 connected to the head 148, and a shank 152 connected to the cylinder 150. The shank 152 may be located at the innermost or inward-facing end of the pivot pins 136, 138. The head 148 of the pivot pins 136, 138 may be received in and retained by the seating opening 164 of the first plate 122. The internal plate 124 may similarly define through openings 166 arranged to receive the shank 152 of each of the pivot pins 136, 138. The internal plate 124 may also define at least one window 154 through which a portion, as in the upper portion, of a retaining member 140a extends.

The first and second pivot pins 136, 138 may be arranged along axes B-B, and the first and second retaining members 140a, 140b may be arranged along axes A-A. As shown, the axes A-A, B-B extend between inner and outer surfaces of the hinge 100 and are generally perpendicular or orthogonal to a range of motion of a hinge, as is common in a polycentric hinge.

Adjacent to the internal plate 124, a first or outer washer 126 may be arranged to receive the first and second pivot pins 136, 138 and to engage with the cylinder 150. A second or inner washer 132 may be arranged for receiving the first and second pivot pins 136, 138 and to facilitate attachment of the first and second pivot pins 136, 138 to the second plate 134, which defines the innermost portion of the hinge 100. The first and second washers 126, 132 define first bearing surfaces 127a, 127b, respectively, and second bearing surfaces 129a, 129b, respectively, that are adapted to and have a corresponding shape relative to inner profiles 111, 113 of the first and second rotation stops 110, 112 so as to interlock therewith.

Figure 3A:
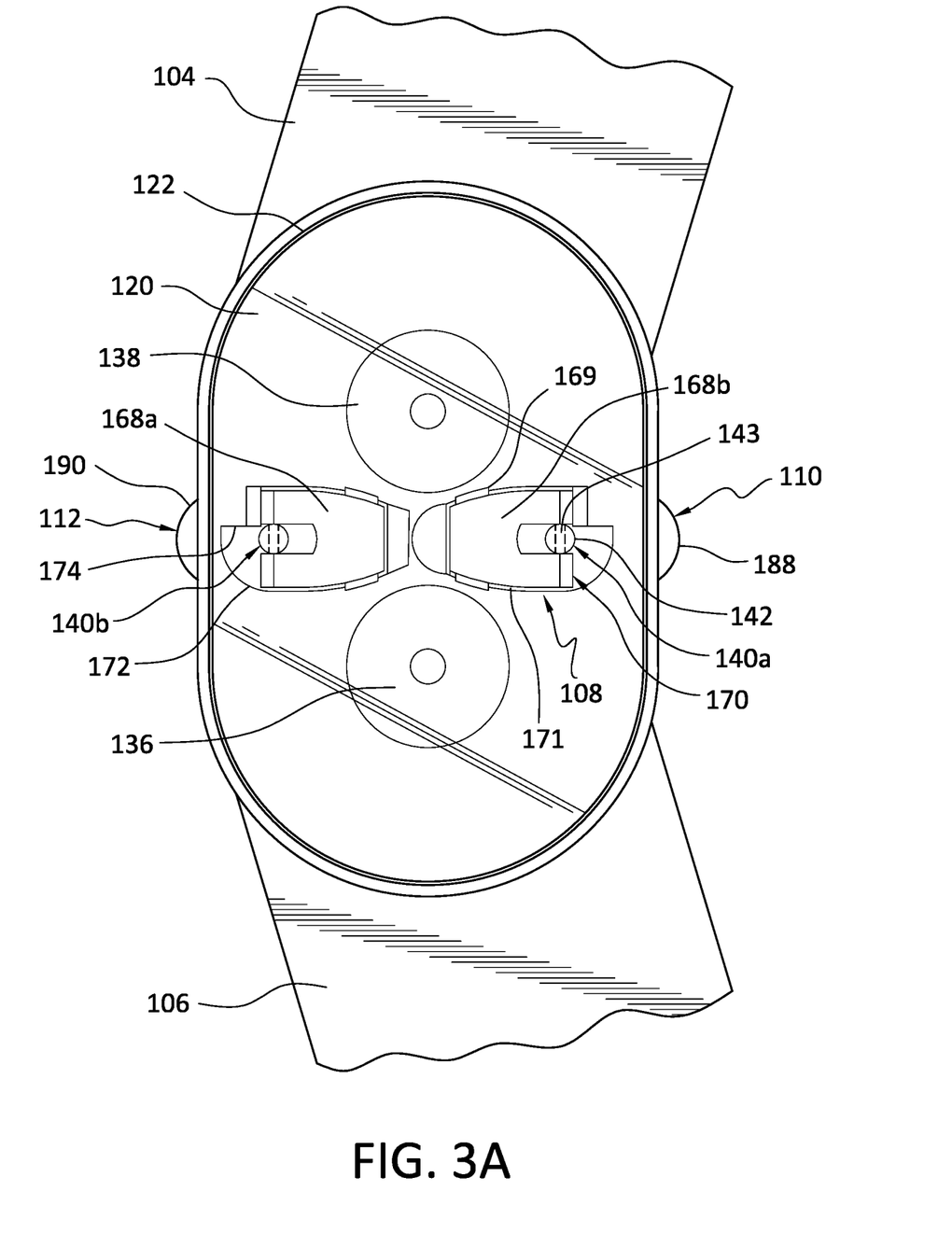
FIG. 3A is a front elevational view of the hinge in FIG. 1 with levers in a closed configuration.
Figure 3B:
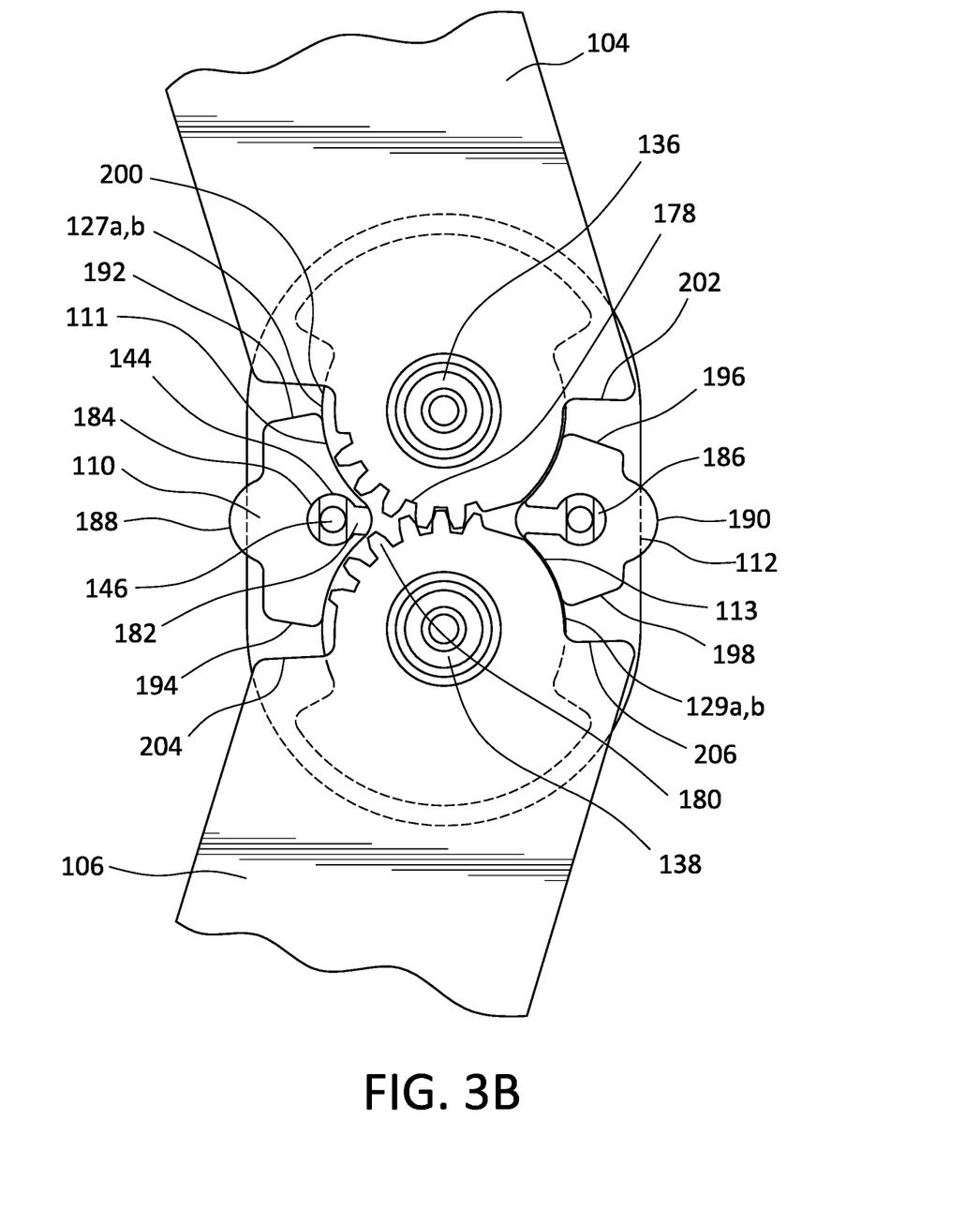
FIG. 3B is a rear elevational view of the hinge in FIG. 1.

As better shown in FIG. 3B, the first and second bearing surfaces 127a, 127b, 129a, 129 are contoured to the inner profiles 111, 113 so the first and second rotation stops 110, 112 are seated in the first and second bearing surfaces 127a, 127b, 129a, 129b when the first and second rotation stops 110, 112 are in the locked configuration. This leads to a snug and stable fitting relative to the components of the hinge 100 and the struts 104, 106, particularly as the rotation stops 110, 112 must be able to stably and without movement limit motion of the struts 104, 106 relative to one another when the hinge 100 and a corresponding device incorporating the hinge 100 is worn by a user.

The first and second bearing surfaces 127a, 127b, 129a, 129b enable the clinician or user to know when the first and second rotation stops 110, 112 are inserted into the hinge 100 in a secure and repeatable manner. The first and second bearing surfaces 127a, 127b, 129a, 129b prevent the first and second rotation stops 110, 112 from interfering with toothed sectors 178, 180 of the struts 104, 106. Due to the corresponding and interlocking profiles of the first and second bearing surfaces 127a, 127b, 129a, 129b relative to the inner profiles 111, 113, the first and second rotation stops 110, 112 are reinforced from movement due to interaction with the struts 104, 106 and limit a range of motion, First and second bearings 128, 130 may be arranged adjacent to and inwardly of the first washer 126. The bearings 128, 130 may be arranged to extend into respective first and second strut openings 156, 158 formed in and by the first and second struts 104, 106, allowing the first and second pivot pins 136, 138 to extend toward an inner or inward-facing side of the hinge 100. The bearings 128, 130 may receive the cylinder portion 150 of the pivot pins 136, 138.

The second plate 134 may define receiving apertures 160 aligned along axes A-A and configured to engage with the second portion 146 of the first and second retaining members 140a, 140b. The second plate 134 may also define receptacles 162 on an outward-facing surface thereof arranged for receiving an end portion of the shank 152 of the first and second pivot pins 136, 138.

In an assembled state, the arrangement of the components of the hinge 100 allows the first and second struts 104, 106 to pivot relative to each other in a controlled manner while providing support at a joint. The components may be arranged to accommodate and cooperate with the insertion of first and second rotation stops 110, 112, which in an embodiment may be applied or inserted laterally, i.e. orthogonally to the axes A-A, B-B.

FIG. 3A depicts in a front elevational view of the hinge 100 the first and second struts 104, 106 joined by the hinge 100 and limited in flexion and extension by the first and second rotation stops 110, 112. The hinge 100 may advantageously facilitate the addition or removal, i.e. engagement or disengagement, of the first and second rotation stops 110, 112 through the provision of locking devices 108 having components that allow a user or clinician to lock or unlock the first and second rotation stops 110, 112. When locked in a locked configuration, the locking devices 108 may be concealed from use and prevented from movement, thereby preventing inadvertent loosening of the rotation stops. While two locking devices 108 are shown, it will be understood that more ore fewer locking devices may be provided as suitable.

The locking devices 108 may comprise levers 168a, 168b attached to the first plate 122 that may be manipulated to lock or unlock the first and second rotation stops 110, 112 in cooperation with the first and second retaining members 140a, 140b. The cover 120 may be arranged to extend over the first plate 122 and secure therewith. By being removably securable to the first plate 122, the cover 120 advantageously may be arranged to conceal the levers 168a, 168b.

Figure 7A:
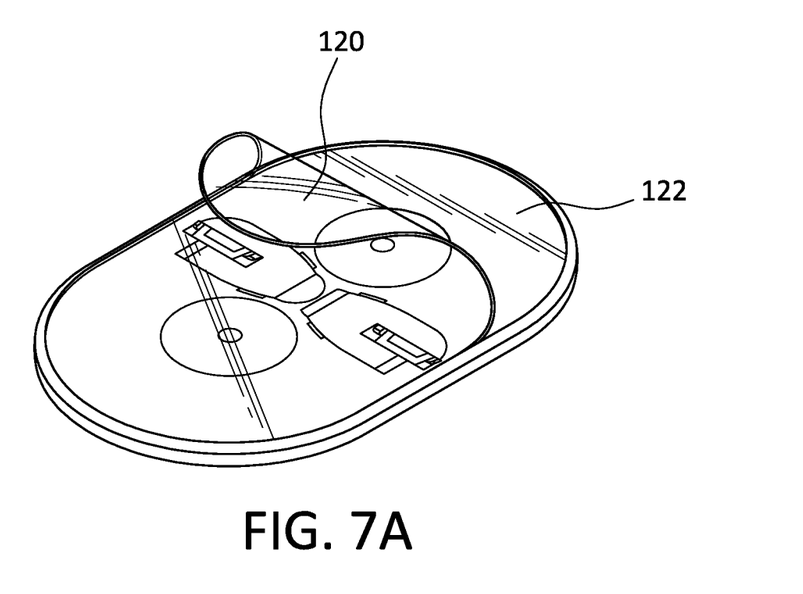
FIG. 7A is a perspective view of a hinge according to an embodiment.

As exemplified in FIG. 7A, the cover 120 may be arranged to be flexibly secured to the first plate 122 and to "peel" away therefrom. In other embodiments, the cover 120 may be interlocked with the first plate 122 to be removably secured therewith.

The levers 168a, 168b may be received in lever recesses 170 defined in a surface of the first plate 122 so in a first locked or concealed configuration, the levers 168a, 168b lie flat against or substantially flush with the first plate 122. This enables the levers 168a, 168b to be concealed when in a locked and concealed configuration, maintaining a minimized profile of the hinge 100. The recesses 170 also protect or prevent the levers 168a, 168b from inadvertent adjustment, as when the levers 168a, 168b are in the recesses 170, they are prevented from flipping outwardly and being rotated.

A profile 169 of the levers 168a, 168b may be arranged to correspond to a first section 171 of the lever recesses 170, when in the locked and concealed configuration. The levers 168a, 168b may be arranged to rotate or flip upward so a user or clinician may grip and rotate the levers 168a, 168b to a second configuration. The levers 168a, 168b may be arranged to rotate through an engagement feature or through hole 148 defined through a body of the retaining members 140a, 140b.

As the levers 168a, 168b rotate when disengaged from the recesses 170 and disposed generally perpendicular to the outer surface of the first plate 122, the levers 168a, 168b may rotate through a second section 172 of the lever recesses 170. The second section 172 may define a substantially arcuate shape, facilitating a rotation of the levers 168a, 168b, until the levers 168a, 168b abut a stop section 174. The stop section 174 may be arranged to correspond to a rotation position at which the first and second rotation stops 110, 112 are unlocked or released. The first and second pivot pins 136, 138 may be arranged so the levers 168a, 168b may rotate freely without interference with or by the pivot pins 136, 138.

The first and second stops 110, 112 may be arranged with tabs 188, 190 respectively, allowing a user or clinician to effectively grip the tabs 188, 190 and remove or insert the rotation stops 110, 112, particularly when the levers 168a, 168b are arranged in an unlocked configuration, as explained in greater detail herein. The tabs 188, 190 may be arranged to slightly protrude from a periphery of the first and second plates 122, 134 to enable easy articulation of the rotation stops 110, 112 when being installed and removed from the hinge 100.

As seen in greater detail in FIG. 3B, the first and second rotation stops 110, 112 operate to limit flexion and extension respectively by engaging the first and second struts 104, 106 along stop surfaces. The first strut 104 may be provided with first and second stop surfaces 200, 202, and the second strut 106 may be provided with first and second stop surfaces 204, 206. The first and second rotation stops 110, 112 and the first and second struts 104, 106 may be arranged in size and shape to provide a controlled degree of flexion and extension by arranging the stop surfaces 200, 202, 204, 206 to abut corresponding stop surfaces on the first and second rotation stops 110, 112 when the desired degree of flexion or extension has been reached. The first rotation stop 110 may define first and second stop surfaces 192, 194, and the second rotation stop 112 may define first and second stop surfaces 196, 198.

The first and second rotation stops 110, 112 may define recesses arranged as receiving sections 184, 186 and passage sections 182 that cooperate with a shape of the retaining members 140a, 140b. The retaining members 140a, 140b may define a first portion 142, an abutment portion 144 extending from the first portion 142 and in contact with a second portion 146 which extends from the abutment portion 144, so the first portion 142, the abutment portion 144, and the second portion 146 are coaxial along axis 5A-5A as shown and described regarding FIG. 5A.

The abutment portion 144 may define a substantially rectangular shape, in that the abutment portion 144 may be longer along one axis than another axis. The first and second rotation stops 110, 112 may be positioned to engage with one of the retaining members 140a, 140b, with the retaining member 140a, 140b and the abutment portion 144 thereof extending within the receiving section 184, 186. The longer axis of the abutment portion 144 may be arranged in a first position, precluding the abutment portion 144 from translating through the passage section 182, thereby retaining the rotation stop 110, 112 in place. In an unlocked configuration, the shorter axis of the abutment portion 144 is translated through the passage section 182, facilitating removal of the rotation stop 110, 112 at the discretion of the user or clinician.

The first and second rotation stops 110, 112 may have a profile that cooperate with the first and second struts 104, 106 by allowing the toothed sectors 178, 180 of the first and second struts 104, 106 respectively to translate freely along the profile of the first and second rotation stops 110, 112. The first and second rotation stops 110, 112 may thereby allow flexion and extension uninhibited within a certain predetermined range. The configuration of and relationship between the rotation stops, retaining members, and other components of the hinge according to the described embodiments is merely exemplary, and any suitable configuration and/or relationship between the components may be used.

Figure 4A:
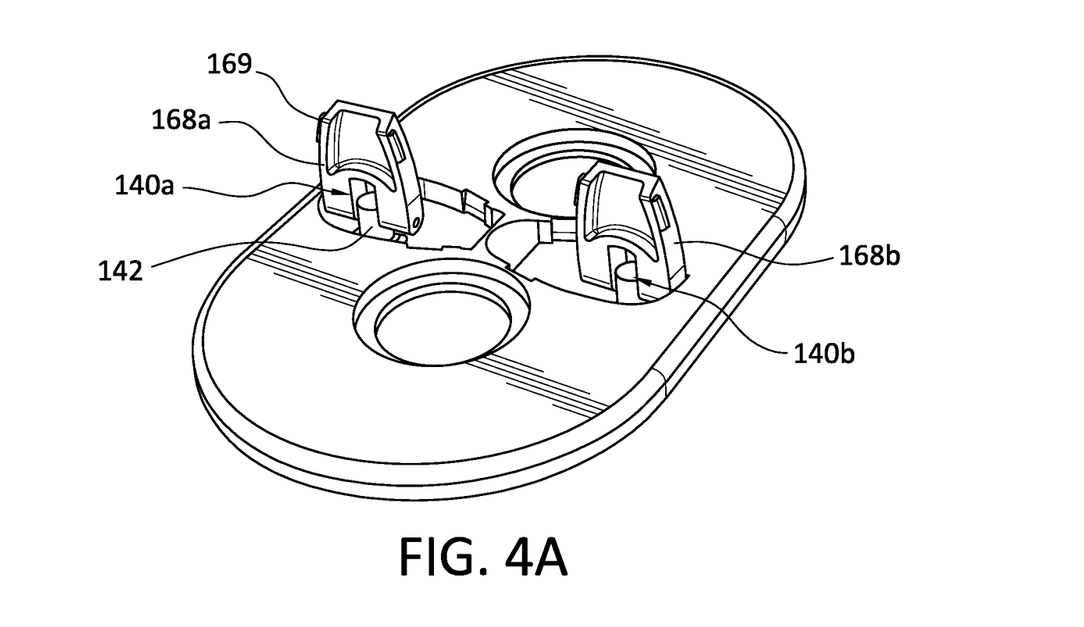
FIG. 4A is a perspective schematic view of the hinge in FIG. 1 with levers in an open configuration.
Figure 4B:
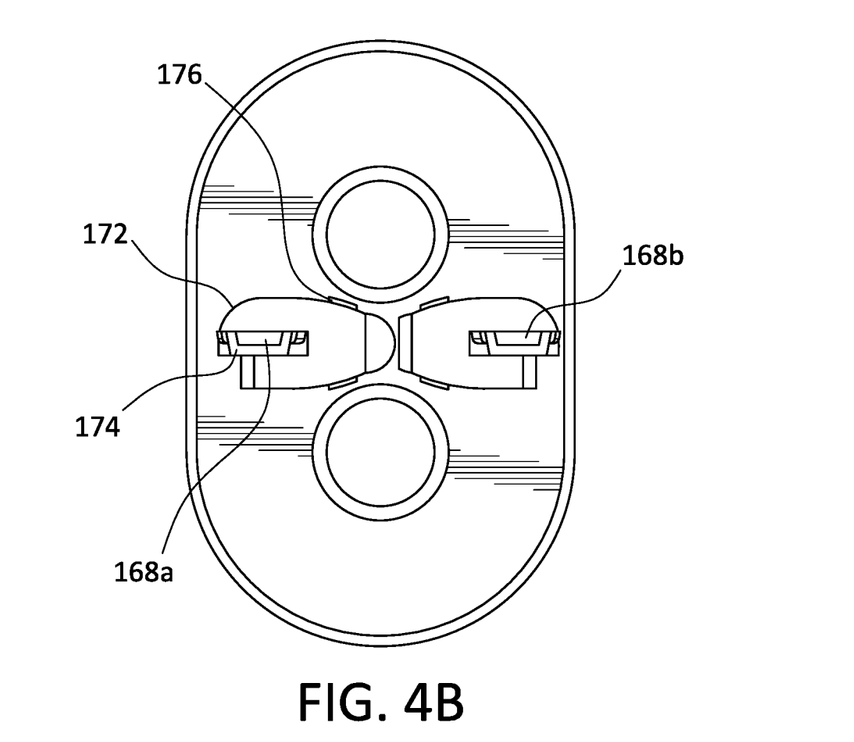
FIG. 4B is an elevational schematic view of the hinge in FIG. 1 with levers in the open configuration.

The operation of the levers 168a, 168b is seen more clearly in the perspective schematic view of FIGS. 4A, 4B. The levers 168a, 168b may be arranged to cooperate with the retaining members 140a, 140b by engaging a first portion 142 of the retaining members 140a, 140b through an engagement feature such as a protrusion (not shown) in a through hole 143 as shown in FIGS. 3A and 5A. The levers 168a, 168b may rotate within or pivot relative to the through hole 143, enabling the levers 168a, 168b to lift or flip up and allowing a user or clinician to easily manipulate and turn the retaining members 140a, 140b between the locked and unlocked configuration, with rotation defined by the lever recesses 170, which define the second section 172 and the stop section 174. The second section 172 may be arcuate so the lever 168a, 168b may rotate to the stop section 174 without interference. The levers 168a, 168b allow for the simple but secure locking and unlocking of the first and second rotation stops 110, 112 within the hinge 100 without the need for a separate tool as in existing hinge devices.

The structure of the retaining members 140a, 140b according to an embodiment is shown in FIGS. 5A-5C. The retaining member 140 may have along a longitudinal axis 5A-5A a first portion 142, an abutment portion 144 attached to the first or upper portion 142, and a second or lower portion 146 attached to the abutment portion 144. The through hole 143 extends through the first portion 142, allowing the levers 168a, 168b to engage the retaining member 140 at an outermost portion of the hinge 100.

In contrast to the abutment portion 144, a non-abutment portion 147 is provided. As described above regarding the embodiment of FIG. 3B, the non-abutment portion 147 may be generally tangent to the periphery of the upper and lower portions 142, 146, as shown in FIGS. 5B and 5C, or may protrude outwardly relative to the periphery of the upper and lower portions 142, 146. In the preferred embodiment, the non-abutment portion 147 is preferably flat to mimic or correspond to the periphery of the passage section 182, which in the preferred embodiment of FIG. 3B comprises opposed, straight surfaces. The second portion 146 of the retaining members 140a, 140b may be rotated within a window 154 formed by the internal plate 124, and the aperture 160 in the second plate 134 receives the second portion 146.

The non-abutment portion 147 may be arranged in an unlocked configuration to translate through the passage section 182 of the rotation stop 110, 112, whereas in a locked configuration the abutment portion 144 is arranged to abut the walls of the corresponding receiving section 184, 186, precluding translation through the passage section 182. An abutment profile 145 may be defined by the abutment portion 144, extending in at least a segment of a periphery of the abutment portion 144 radially relative to the upper portion and the lower portion 142, 146, and allowing the abutment portion 144 to cooperate with a shape of the receiving section 184, 186, which in an embodiment may define an arcuate shape, although other suitable shapes may be used.

Figure 6A:
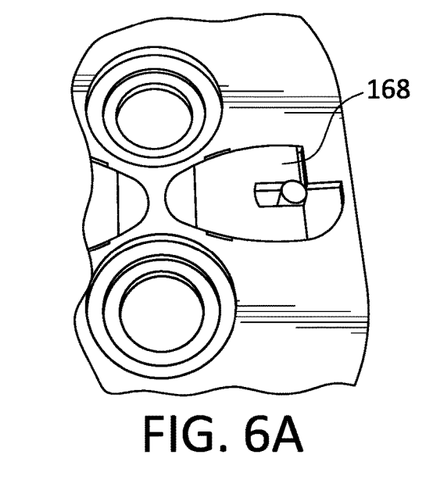
FIG. 6A is a schematic view of the lever in a closed configuration.
Figure 6B:
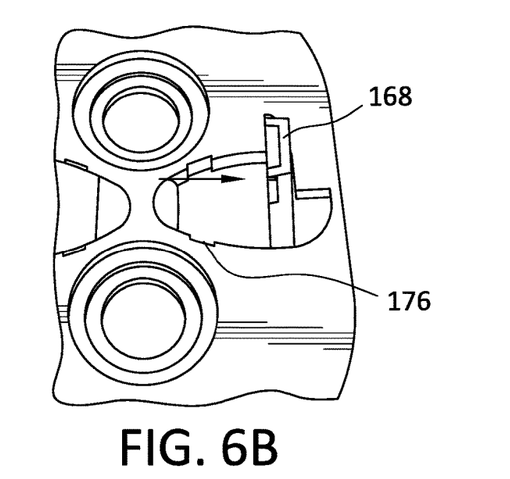
FIG. 6B is a schematic view of opening the lever from the closed configuration to the open configuration.
Figure 6C:
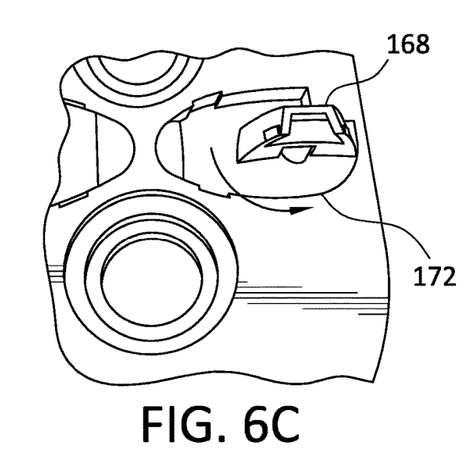
FIG. 6C is a schematic view of turning the lever from a locked configuration to an unlocked configuration.
Figure 6D:
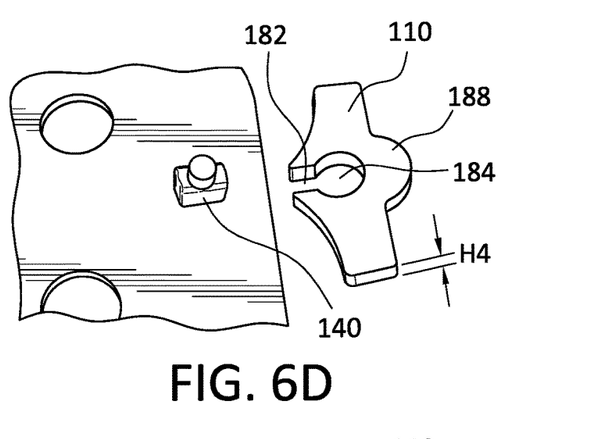
FIG. 6D is a schematic view of installing a rotation stop to the retaining member of FIG. 5A in the unlocked configuration.
Figure 6E:
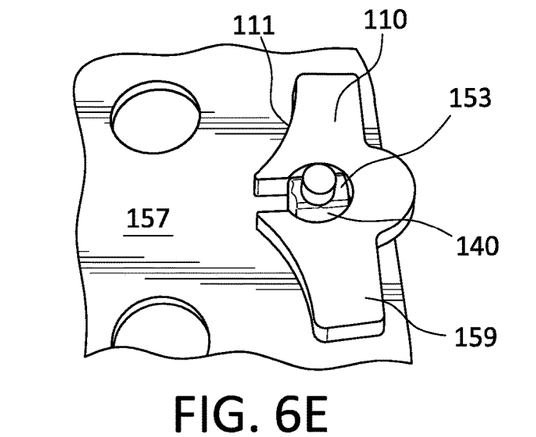
FIG. 6E is a schematic view of the retaining member installed on the rotation stop in the unlocked configuration.
Figure 6F:
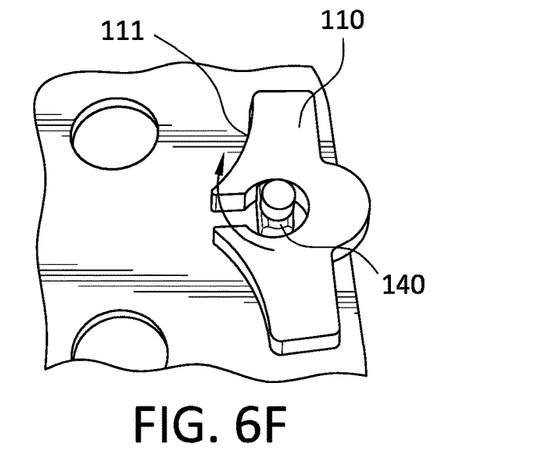
FIG. 6F is a schematic view of the retaining member installed on the rotation stop in the locked configuration.

To illustrate the abutment portion 144 relative to the non-abutment portion 147, in the preferred embodiment of FIG. 5A, the abutment portion 144 has generally flat first and second surfaces 153, 155, generally perpendicular or perpendicular relative to the axis 5A-5A. From the configuration of the first and second surfaces 153, 155, they can align flush with surfaces of the hinge 100, such as with a surface 157 of the second plate 134 shown in FIG. 6E. Likewise, the first and second surfaces may align flush with a surface of the first plate 122 or the inner plate 124.

FIGS. 5A-5C illustrate the abutment portion 144 as having opposed arcuate surfaces 149a, 149b, and the non-abutment portion 147 has opposed generally flat and parallel surfaces 151a, 151b. As the arcuate surfaces 149a, 149b are curved with a radius relative to the axis 5A-5A, they extend a radius R1 from the axis 5A-5A, are generally equidistant therefrom. At least the first portion 142 has a circular cross-section and a radius R2 and corresponding diameter D1. The arcuate surfaces 149a, 149b extend a distance L3 from the first portion 142, and is defined as the extent of abutment profile combined with the arcuate surfaces 149a, 149b and a height H2 of the abutment portion 144. The length L1 of the abutment portion 144 comprises the diameter D1 of the first portion 142, and the pair of distances L3 on opposed sides of the abutment portion 144 extending in the first direction d1, intersecting the axis 5A-5A and bisecting the arcuate surfaces 149a, 149b. The first and second portions 142, 146 may have the same radius R2, and are coaxial relative to one another.

The non-abutment portion 147 may have a length L2 extending in a second direction d2 generally perpendicular to the first direction d1. The length L2 may comprise the diameter D1 of the first portion 142, or may extend radially beyond diameter D1. As the arcuate surfaces 149a, 149 have a curvature, the surfaces 151a, 151b are flat and arranged generally perpendicularly to the second direction d2 or parallel to direction d1 to facilitate sliding in and out of an opening of the rotation stop 110, 112 leading to a passage section. A width W1 of the abutment profile 145 can be less than a width W2 of the surfaces 151a, 151b defining a non-abutment profile.

As shown in FIG. 5C, the first portion 142 has a height H1 that is greater than a height H2 of the abutment portion 144, which is greater than a height H3 of the second portion 146. The combined heights H1, H2, H3 result in a total height HT of the retaining member 140. The non-abutment portion 147 is preferably located opposite the abutment portion 144 along a same segment of the axis 5A-5A of the retaining member 140a, 140b.

The depicted configurations are merely exemplary, and a retaining member according to the disclosure may have any suitable configuration.

FIGS. 6A-6F illustrate the operation of the hinge 100. A lever 168 may be arranged within a locked profile 176 to lay substantially flat or flush within a recess in a cover plate of the hinge. The lever 168 may be shaped to be lifted or rotated upward relative to the cover plate, and to be rotated within the recess of the cover plate along an arcuate profile 172. The rotation of the lever 168 along the arcuate profile 172 may rotate a retaining member 140 to an unlocked configuration, so a rotation stop 110 defining a receiving section and a passage section can disengage from the retaining member 140.

The rotation stop 110 may have a height H4 that is the same as the height H2 of the abutment portion 144. The first surface 153 may be generally parallel with a first surface 159 of the rotation stop.

When the rotation stop 110 or a different stop is to be inserted, a passage section 182 may insert the rotation stop 110 such that the retaining member 140 extends within a receiving section 184. The bearing surface of the bearing (shown in FIGS. 2 and 3B), is abutted by the inner profile 111 of the rotation stop 110, assuring the rotation stop 110 is inserted within the hinge. Rotation of the retaining member 140 by the lever 168 may arrange the retaining member 140 so an abutment portion, having a longer axis may preclude translation through the receiving section of the rotation stop 110, locking the rotation stop 110 in place. The tab 188 extends a distance outside of the hinge 100 to facilitate repeated removal and insertion of the rotation stop 110 within the hinge 100. All of the steps depicted in FIGS. 6A-6F may advantageously be completed with no use of external and/or dedicated tools.

Figure 7B:
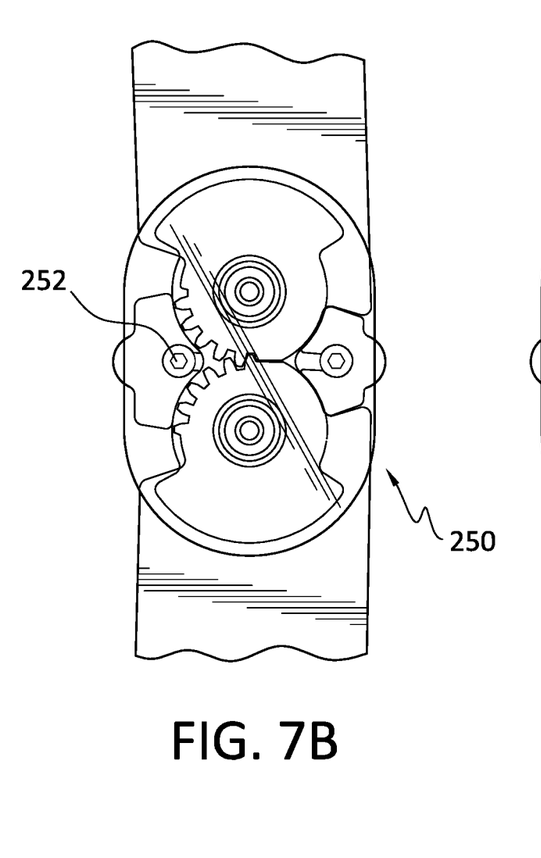
FIG. 7B is a top plan view of a hinge according to another embodiment.
Figure 7C:
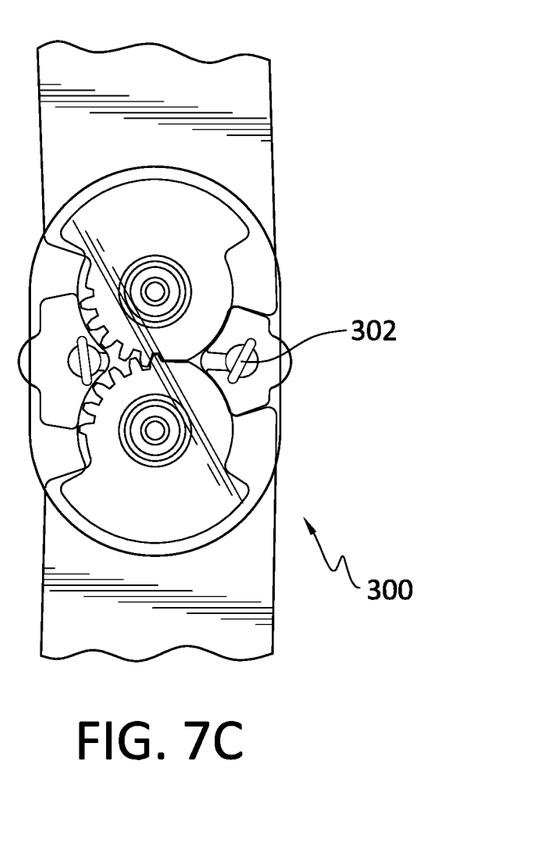
FIG. 7C is a top plan view of a hinge according to another embodiment.

As seen in the embodiments of FIGS. 7A-7C, a cover plate 120 may be clear and/or translucent and arranged over the first plate 122 such that a user or clinician may observe the status and orientation of the first and second rotation stops 110, 112, facilitating easier and more intuitive operation of the hinge 100. The cover 120 may be removable and may be formed of any suitable material.

In FIG. 7B, an alternative arrangement of a hinge 250 is depicted, with set screws 252 retaining the rotation stops in place. As with the first and second rotation stops 110, 112 and levers 168a, 168b, the set screws 252 may facilitate easy and intuitive addition or removal of the rotation stops without the need for or use of external and/or dedicated tools. In FIG. 7C, a hinge 300 may instead use levers 302 that toggle between a locked or unlocked configuration to facilitate addition or removal of rotation stops.

The hinge having a rotation-stop lock and components provided therewith have improved adjustability and customization of a hinge for users by providing controlled ranges of flexion and extension that do not require the use of tools to adjust, and do not require that the hinge be disassembled to provide said adjustments. The hinge of the disclosed embodiments thus advantageously addresses the problem of existing hinges being difficult to adjust by both users and clinicians as the rotation stop may be difficult to add or remove from the hinge.

It is to be understood that not necessarily all objects or advantages may be achieved under any embodiment of the disclosure. Those skilled in the art will recognize that the hinge may be embodied or carried out so it achieves or optimizes one advantage or group of advantages as taught herein without necessarily achieving other objects or advantages as taught herein.

The skilled artisan will recognize the interchangeability of various disclosed features. Besides the variations described, other known equivalents for each feature can be mixed and matched by one of ordinary skill in this art to construct a hinge under principles of the present disclosure. It will be understood by the skilled artisan that the features described may be adapted to other types of devices. Hence this disclosure and the embodiments and variations thereof are not limited to hinges for orthopedic devices but can be utilized in any devices.

Although this disclosure describes certain exemplary embodiments and examples of a hinge, it will be understood by those skilled in the art that the present disclosure extends beyond the specifically disclosed embodiments to other alternative embodiments and/or uses of the disclosure and obvious modifications and equivalents thereof. It is intended that the present disclosure should not be limited by the disclosed embodiments described above and may be extended to other applications that may employ the features described.

The invention claimed is:

1. A hinge configured for selectively retaining and removing at least one rotation stop without a supplementary tool, the hinge comprising:
   a hinge assembly comprising a locking device having at least one lever arranged to selectively rotate a retaining member for engagement and disengagement with the at least one rotation stop, the retaining member forming an abutment portion extending from a first portion and a second portion extending from the abutment portion, the first portion, the abutment portion, and the second portion extending coaxial relative to one another along a first axis;
   wherein the abutment portion defines an abutment profile protruding outwardly at least a length beyond the first portion and the second portion about at least one segment of a periphery of the abutment portion, the abutment portion defines a non-abutment profile located outside the abutment profile in at least another segment of the periphery of the abutment portion and defines a width corresponding to a width of the first and second portions;
   first and second struts connected to the hinge assembly, the at least one rotation stop limiting a range of motion of the first strut relative to the second strut;
   first and second pivot pins extending through strut openings formed by the first and second struts, respectively;
   an internal plate located between the first plate and the first and second struts, the internal plate having openings through which the first and second pivot pins pass.

2. The hinge of claim 1, further comprising a first plate at which the at least one lever is located.

3. The hinge of claim 1, further comprising a cover adapted to extend over the first plate and removably secure therewith, thereby concealing the at least one lever.

4. The hinge of claim 1, wherein the first and second pivot pins each have a head retained by a seated opening of the first plate.

5. The hinge of claim 4, wherein the first and second pivot pins each have a cylinder portion depending from the head, each cylinder portion being received by a bearing within the strut openings.

6. The hinge of claim 1, wherein the internal plate forms a window through which the second portion of the at least one retaining member rotates.

7. A hinge configured for selectively retaining and removing at least one rotation stop without a supplementary tool, the hinge comprising:
   a hinge assembly comprising a locking device having at least one lever arranged to selectively rotate a retaining member for engagement and disengagement with the at least one rotation stop, the retaining member forming an abutment portion extending from a first portion and a second portion extending from the abutment portion, the first portion, the abutment portion, and the second portion extending coaxial relative to one another along a first axis;
   wherein the abutment portion defines an abutment profile protruding outwardly at least a length beyond the first portion and the second portion about at least one segment of a periphery of the abutment portion, the abutment portion defines a non-abutment profile located outside the abutment profile in at least another segment of the periphery of the abutment portion and defines a width corresponding to a width of the first and second portions;
   first and second struts connected to the hinge assembly, the at least one rotation stop limiting a range of motion of the first strut relative to the second strut;
   first and second pivot pins extending through strut openings formed by the first and second struts, respectively;
   an outer washer plate located on a first side of the first and second struts, and an inner washer plate located on a second side of the first and second struts.

8. The hinge of claim 7, further comprising a second plate in which the inner washer plate is located between the second plate and the second side of the first and second struts.

9. The hinge of claim 8, wherein the second plate defines receptacles for receiving an end portion of a shank of the first and second pivot pins.

10. The hinge of claim 8, wherein the second plate forms an aperture arranged to receive the second portion of the retaining member.

11. The hinge of claim 1, wherein the at least one lever is pivotally connected to the retaining member by an engagement feature.

12. The hinge of claim 1, wherein the at least one lever has a lever profile generally corresponding in shape to a first section.

13. A hinge configured for selectively retaining and removing at least one rotation stop without a supplementary tool, the hinge comprising:
   a first plate having at least one lever recess defined along an outer surface of the first plate;
   a locking device having at least one lever arranged to selectively rotate a retaining member for engagement and disengagement with the at least one rotation stop, the retaining member forming an abutment portion extending from a first portion and a second portion extending from the abutment portion, the first portion, the abutment portion, and the second portion extending coaxial relative to one another along a first axis;
   wherein the abutment portion defines an abutment profile protruding outwardly at least a length beyond the first portion and the second portion about at least one segment of a periphery of the abutment portion, the abutment portion defines a non-abutment profile located outside the abutment profile in at least another segment of the periphery of the abutment portion and defines a width corresponding to a width of the first and second portions;

wherein in a first configuration, the at least one lever is received in the at least one lever recess in that the at least one lever lies at least substantially flush with the outer surface of the first plate, a profile of the at least one lever is arranged to correspond to a first section of the at least one lever recess, the at least one lever is arranged to move upward from the at least one lever recess to position the at least one lever to a second configuration for permitting disengagement of the abutment portion from the at least one rotation stop.

14. The hinge of claim 13, wherein in the second configuration, the at least one lever is arranged generally perpendicular to the outer surface of the first plate, and is rotatable through a second section of the at least one lever recess.

15. The hinge of claim 14, wherein the second section of the at least one lever recess defines a generally arcuate shape, and forms a stop section preventing further rotation of the at least one lever, when the at least one lever is rotated to the stop section, the non-abutment profile aligns with an opening of the at least one rotation stop permitting removal from the retaining member.

16. A hinge comprising:
a first plate having at least one lever recess defined along an outer surface of the first plate;
a rotation stop having an opening defining a receiving section and a passage section extending from the receiving section to open along a periphery of the rotation stop, the passage section being more narrow than the receiving section;
a locking device having at least one lever arranged to selectively rotate a retaining member for engagement and disengagement with the rotation stop, the retaining member forming an abutment portion extending from a first portion and a second portion extending from the abutment portion, the first portion, the abutment portion, and the second portion extending coaxial relative to one another along a first axis;

wherein the abutment portion defines an abutment profile protruding outwardly at least a length beyond the first portion and the second portion about at least one segment of a periphery of the abutment portion, the abutment portion defines a non-abutment profile located outside the abutment profile in at least another segment of the periphery of the abutment portion and defines a width corresponding to a width of the first and second portions;

wherein the narrow section of the rotation stop is configured and dimensioned to permit passage of the abutment portion to slide therethrough when the non-abutment profile is aligned to the passage section in a first configuration of the locking device, when the abutment portion is rotated relative to the first configuration to a second configuration, the abutment profile prevents sliding of the abutment portion relative to the passage section, the abutment profile is configured and dimensioned differently from the non-abutment profile and is arranged to be received by the receiving section of the rotation stop.

17. The hinge of claim 16, wherein the abutment portion defines a substantially rectangular shape, in that the abutment profile extends in a first direction longer than a second direction perpendicular to the first direction, the second direction corresponding to the non-abutment profile, the non-abutment profile having a width generally the same as the passage section of the opening of the rotation stop.

* * * * *